United States Patent
Xu et al.

(10) Patent No.: US 11,649,263 B2
(45) Date of Patent: May 16, 2023

(54) METHODS AND APPARATUS FOR SIMULTANEOUSLY DETECTING A LARGE RANGE OF PROTEIN CONCENTRATIONS

(71) Applicant: ProteinSimple, San Jose, CA (US)

(72) Inventors: Hui Xu, Palo Alto, CA (US); Kenneth Swartz, Los Gatos, CA (US)

(73) Assignee: ProteinSimple, San Jose, CA (US)

(*) Notice: Subject to any disclaimer, the term of this patent is extended or adjusted under 35 U.S.C. 154(b) by 716 days.

(21) Appl. No.: 16/423,787

(22) Filed: May 28, 2019

(65) Prior Publication Data

US 2019/0285551 A1   Sep. 19, 2019

Related U.S. Application Data

(63) Continuation of application No. PCT/US2017/063704, filed on Nov. 29, 2017.
(Continued)

(51) Int. Cl.
*G01N 21/76* (2006.01)
*C07K 1/26* (2006.01)
(Continued)

(52) U.S. Cl.
CPC .................. *C07K 1/26* (2013.01); *C07K 1/28* (2013.01); *G01N 1/20* (2013.01); *G01N 1/40* (2013.01);
(Continued)

(58) Field of Classification Search
CPC ............ G01N 21/76; G01N 1/20; G01N 1/40; G01N 33/54366; G01N 33/6803;
(Continued)

(56) References Cited

U.S. PATENT DOCUMENTS 6,148,060 A   11/2000  Collins et al.
6,230,975 B1   5/2001  Colley et al.
(Continued)

FOREIGN PATENT DOCUMENTS

CN   1791680 A    6/2006
CN   104459008 A  3/2015
(Continued)

OTHER PUBLICATIONS

Debevec, P. E. et al., "Recovering High Dynamic Range Radiance Maps from Photographs," In Proceedings of the 24th Annual Conference on Computer Graphics and Interactive Techniques, Aug. 3, 1997, pp. 369-378.
(Continued)

*Primary Examiner* — Christopher L Chin
(74) *Attorney, Agent, or Firm* — Cooley LLP (57) ABSTRACT

Some embodiments described herein relate to a method that includes separating an analyte-containing sample via electrophoresis in a capillary. The capillary is loaded with a chemiluminescence agent, such as luminol, that is configured to react with the analyte (e.g., HRP-conjugated proteins) to produce a signal indicative of a concentration and/or quantity of analyte at each location along the length of the capillary. A first image of the capillary containing the analytes and the chemiluminescence agent is captured over a first period of time. A second image of the capillary containing the analytes and the chemiluminescence agent is captured over a second, longer, period of time. A concentration and/or quantity of a first population of analytes at a first location is determined using the first image, and a concentration and/or quantity of a second population of analytes at a second location is determined using the second image.

20 Claims, 4 Drawing Sheets

Related U.S. Application Data (60) Provisional application No. 62/427,624, filed on Nov. 29, 2016.

(51) Int. Cl.
| | |
|---|---|
| *G01N 1/40* | (2006.01) |
| *G01N 33/543* | (2006.01) |
| *G01N 33/68* | (2006.01) |
| *C07K 1/28* | (2006.01) |
| *G01N 1/20* | (2006.01) |
| *G06V 10/141* | (2022.01) |
| *G06V 10/50* | (2022.01) |
| *G06V 20/69* | (2022.01) |
| *G01N 21/17* | (2006.01) |
| *G01N 27/447* | (2006.01) |
| *G06V 10/10* | (2022.01) |

(52) U.S. Cl.
CPC ....... *G01N 21/76* (2013.01); *G01N 33/54366* (2013.01); *G01N 33/6803* (2013.01); *G06V 10/141* (2022.01); *G06V 10/507* (2022.01); *G06V 20/693* (2022.01); *G06V 20/695* (2022.01); *G01N 27/44721* (2013.01); *G01N 2001/4038* (2013.01); *G01N 2021/1765* (2013.01); *G06V 10/16* (2022.01)

(58) Field of Classification Search
CPC ..... G01N 27/44721; G01N 2001/4038; G01N 2021/1765; G01N 27/44726; G01N 27/44704; C07K 1/26; C07K 1/28; G06V 10/16; G06V 10/141; G06V 10/507; G06V 20/693; G06V 20/695; H04N 4/2355
USPC ........ 204/451, 455, 450, 601; 436/172, 515, 436/516, 116; 530/412; 435/7.1; 348/229.1
See application file for complete search history.

(56) References Cited

U.S. PATENT DOCUMENTS

| | | | | |
|---|---|---|---|---|
| 6,579,722 | B1* | 6/2003 | Collins | G01N 33/0047 436/116 |
| 7,038,820 | B1* | 5/2006 | Kindt | H04N 5/2351 358/475 |
| 2003/0078737 | A1* | 4/2003 | Keys | G01N 21/76 435/7.1 |
| 2003/0134431 | A1* | 7/2003 | Parce | G01N 33/5064 435/287.2 |
| 2004/0095472 | A1 | 5/2004 | Yoshida et al. | |
| 2013/0208138 | A1* | 8/2013 | Li | H04N 5/2355 348/229.1 |
| 2015/0090591 | A1* | 4/2015 | Yang | G01N 27/44704 204/601 |

FOREIGN PATENT DOCUMENTS

| | | |
|---|---|---|
| EP | 3062147 A1 | 8/2016 |
| JP | H10508133 A | 8/1998 |
| JP | 2004007298 A | 1/2004 |
| JP | 2016161653 A | 9/2016 |
| JP | 2016535280 A | 11/2016 |
| WO | WO-2006132666 A1 | 12/2006 |
| WO | WO-2015048458 A2 | 4/2015 |

OTHER PUBLICATIONS

Extended European Search Report for European Application No. 17875646.6, dated Jun. 29, 2020, 8 pages.

First Office Action for Chinese Application No. 201780073354.0, dated Oct. 30, 2020, 24 pages.

International Search Report and Written Opinion for International Application No. PCT/US2017/063704, mailed Mar. 12, 2018, 18 pages.

Jinno, T. et al., "Multiple Exposure Fusion for High Dynamic Range Image Acquisition," IEEE Transactions on Image Processing, vol. 21, No. 1, pp. pp. 358-365, Jan. 2012.

Michels D.A., et al., "Charge Heterogeneity of Monoclonal Antibodies by Multiplexed Imaged Capillary Isoelectric Focusing Immunoassay With Chemiluminescence Detection," Analytical Chemistry, Jun. 2012, vol. 84(12), pp. 5380-5386.

Notice of Reasons for Rejection for Japanese Application No. 2019-520577, dated May 6, 2022, 6 pages.

Notice of Reasons for Rejection for Japanese Application No. 2019-520577, dated Oct. 18, 2021, 11 pages.

Xu, X. et al., "Determination of Three Major Catecholamines in Human Urine by Capillary Zone Electrophoresis with Chemiluminescence Detection," Analytical Biochemistry, vol. 427, No. 1, pp. 10-17, Aug. 2012.

\* cited by examiner

METHODS AND APPARATUS FOR SIMULTANEOUSLY DETECTING A LARGE RANGE OF PROTEIN CONCENTRATIONS

CROSS-REFERENCE TO RELATED APPLICATIONS

This application is a continuation of International Application Number PCT/US2017/063704, filed Nov. 29, 2017, which claims priority to U.S. Provisional Application No. 62/427,624, filed Nov. 29, 2016, the disclosure of which is hereby incorporated by reference in its entirety.

BACKGROUND

A number of known techniques and instruments are suitable for separating proteins chromatographically and electrophoretically. For example, U.S. Pat. Nos. 9,304,133 and 9,400,277, each entitled "Methods and Devices for Analyte Detection," the disclosure of each of which is hereby incorporated by reference in its entirety, describe the separation of proteins via capillary electrophoresis.

In some instances, it can be necessary or desirable to determine a quantity and/or concentration of analytes at one or more locations. Some known methods exist to measure a quantity and/or concentration of analytes using enhanced chemiluminescence (ECL) techniques. For example, the amount of protein captured on the inside walls of the capillary can be measured using an antibody with a horseradish peroxidase (HRP) enzyme that reacts with luminol within the capillary to produce a chemiluminescence signal that can be measured in units of photons/second and/or detections per second.

Traditional ECL techniques include loading a capillary with luminol and capturing one or more images of the capillary as HRP-conjugated proteins reacting with luminol. Traditional ECL techniques may be suitable in situations where each peak contains a similar quantity of protein and/or where the separation results in a single peak. Traditional ECL techniques, however, have poor dynamic range. Similarly stated, traditional ECL techniques are not suitable in situations where separation produces multiple peaks and at least two peaks contain significantly different quantities of protein. In such a situation, peaks with higher concentrations of protein will saturate and/or blind the detector, the peak with the higher concentration will consume all available luminol, and/or peaks with the lower concentrations of protein will not be detectable any of which will reduce the accuracy with which quantities and/or concentrations of protein can be determined. A need therefore exists for methods and apparatus for simultaneously detecting a large range of protein quantities and/or concentrations.

DETAILED DESCRIPTION

A particular problem in quantifying protein contained in multiple techniques using ECL techniques is the selection of an appropriate exposure time for imaging the capillary. Too short an exposure time, and peaks having a low quantity and/or concentration of protein may not be detectable and/or may not be accurately quantifiable. Too long an exposure time, and peaks having a high quantity and/or concentration of protein may saturate and/or blind the detector, wash out nearby peaks, and/or consume all available luminol. One available compromise solution is to take a number of relatively short exposures sequentially. The intensity for each peak can then be plotted versus time, and an initial intensity (e.g., as measured in photons per second) can be extrapolated using a mathematical model of the expected variation of the signal vs time. A concentration and/or quantity of protein at the peak can be determined based on the initial intensity. Such a technique, however, may produce significant statistical errors for small protein concentrations and systemic errors for large protein concentrations.

Some embodiments described herein relate to a method that includes separating an analyte-containing sample via electrophoresis in a capillary. The capillary is loaded with a chemiluminescence agent, such as luminol, that is configured to react with the analyte (e.g., HRP-conjugated proteins) to produce a signal indicative of a concentration and/or quantity of analyte at each location along the length of the capillary. A first image of the capillary containing the analytes and the chemiluminescence agent is captured over a first period of time. A second image of the capillary containing the analytes and the chemiluminescence agent is captured over a second period of time. The second period of time is longer than the first period of time. Similarly stated, the second image of the capillary has a longer exposure time than the first image of the capillary. A concentration and/or quantity of a first population of analytes at a first location is determined using the first image, and a concentration and/or quantity of a second population of analytes at a second location is determined using the second image. In some embodiments, the method can be used with a chromogenic detection agent instead of a chemiluminescence agent.

Some embodiments described herein relate to a method that includes separating a sample that contains a first population of analytes and a second population of analytes via capillary electrophoresis. Separating the sample can result in the first population of analytes migrating to a first position along the length of the capillary and the second population of analytes migrating to a second position along the length of the capillary. Images of the capillary having different exposure times are captured. A first image can be selected in which a strength of a first optical signal that is indicative of a concentration and/or quantity of the first population of analytes exceeds a predetermined threshold. An initial intensity of the first optical signal can be determined by dividing the strength of the first optical signal as detected in the first image by the exposure time of the first image. The initial intensity of the first optical signal can be used to calculate a concentration and/or quantity of the first population of analytes. A second image can be selected in which a strength of a second optical signal exceed the predetermined threshold (e.g., the same predetermined threshold). An initial intensity of the second optical signal can be determined by dividing the strength of the second optical signal as detected in the second image by the exposure time of the second image. The initial intensity of the second optical signal can be used to calculate a concentration and/or quantity of the second population of analytes.

Some embodiments described herein relate to an apparatus configured to effect electrophoretic separation of multiple of populations of analytes (e.g., proteins) that are disposed in a capillary. A detector is configured to capture images of a multiple locations along a length of the capillary. Similarly stated, the detector can be operable to perform full-column imaging of the capillary. A computing entity (e.g., a processor and/or a memory) is configured to select a first image captured by the detector based on an intensity of a first signal at a first location along the length of the capillary exceeding a predetermined threshold. The intensity of the first signal is indicative of a concentration and/or quantity of a first population of analytes that is located at the first location. A concentration and/or quantity of the first population of the analyte can be calculated, for example, based on the intensity of the first signal. A second image captured by the detector can be selected based on an intensity of a second signal at a second location along the length of the capillary exceeding a predetermined threshold (e.g., the same predetermined threshold). The second image can have an exposure time that is different from an exposure time of the first image. The intensity of the second signal is indicative of a concentration and/or quantity of a second population of analytes that is located at the second location. A concentration and/or quantity of the second population of the analyte can be calculated, for example, based on the intensity of the second signal and the second exposure time.

Figure 1:
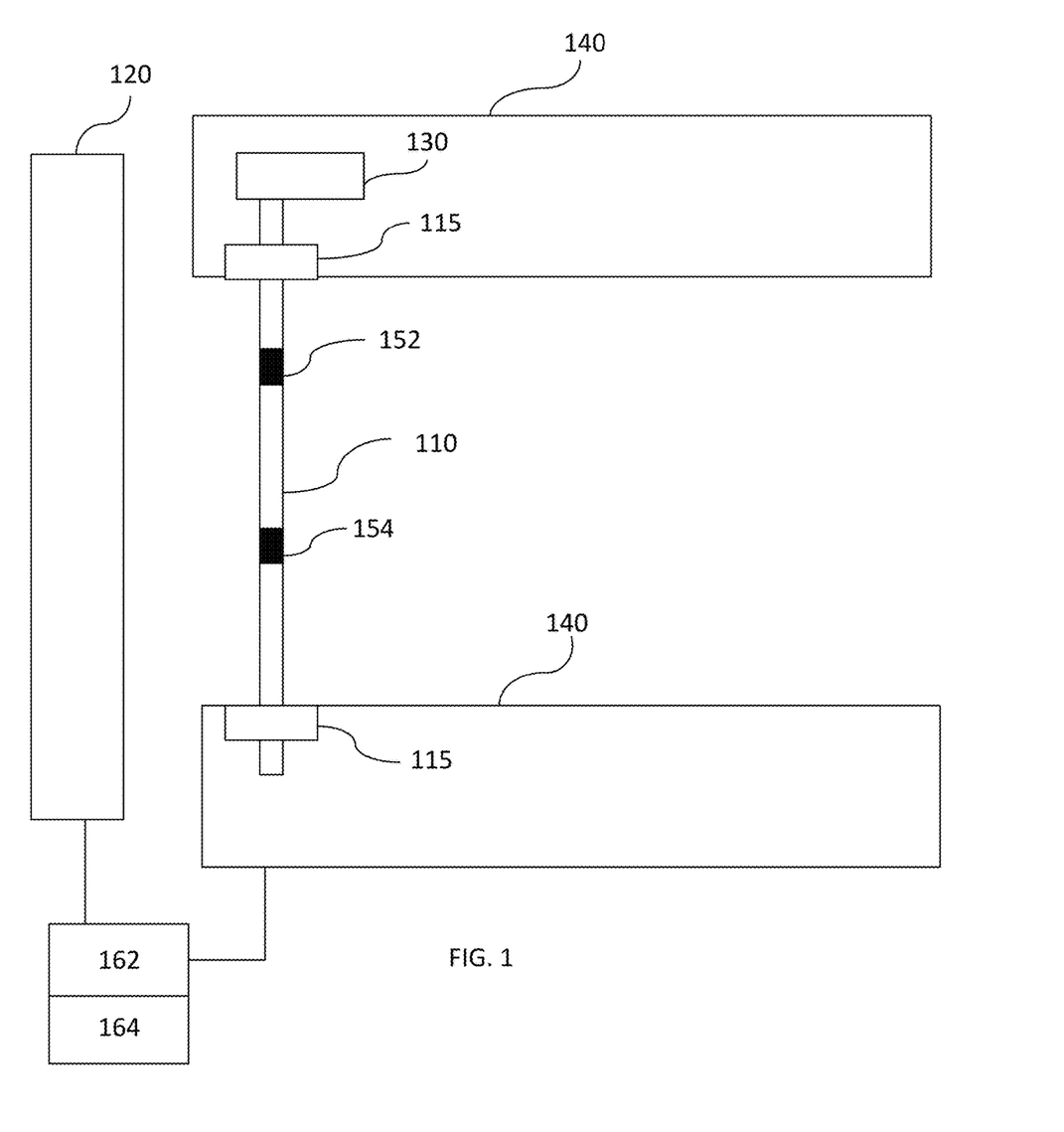
FIG. 1 is a schematic diagram of an instrument operable to measure a large range of analyte quantities and/or concentrations, according to an embodiment.

FIG. 1 is a schematic illustration of an instrument for measuring concentrations and/or quantities of analytes (e.g., proteins), according to an embodiment. The instrument includes a capillary 110, electrodes 115, and a detector 120. The capillary 110 can bridge two reservoirs 140. Each reservoir can be, for example, an anolyte reservoir, a catholyte reservoir, and/or a sample reservoir.

The instrument can be configured to draw a sample containing analytes into the capillary 110 or otherwise accept a capillary 110 containing a sample. An electric potential can be applied across the capillary 110 via the electrodes 115, which can effect an electrophoretic separation of the sample. Similarly stated, populations of the analyte can migrate to different locations along the capillary 110 as a result of an electric potential being applied by the electrodes 115. Populations of analytes having a similar property (e.g., mobility, isoelectric point, etc.) can form peaks or bands in the capillary 110.

As discussed in further detail herein, the instrument can determine a concentration and/or quantity of an analyte in each peak. In some instances a first peak 152 at a first location of the capillary 110 can include a significantly higher quantity and/or concentration of analytes than a second peak 154 at a second location of the capillary 110. Similarly stated, the first peak 152 can include 3 times, 5 times, 10 times, 50 times, 100 times, or more analyte than the second peak 154.

The detector 120 (e.g., a camera, a charge-coupled device (CCD), a complementary metal-oxide-semiconductor (CMOS) detector, etc.) is configured to capture images of the capillary 110, analyte within the capillary 110, and/or photons emitted by an ECL reaction within the capillary 110. The detector 120 can be a full column detector. Similarly stated, the detector 120 can be operable to capture an entire length of the capillary 110, a substantial portion (e.g., at least 80%) of the length of the capillary 110, the entire separation region of the capillary 110, and/or to capture an image that contains at least two different locations separated along a length of the capillary (e.g., locations associated with the first peak 152 and the second peak 154).

A processor 162 and a memory 164 are communicatively coupled to the detector 120. The processor 162 and the memory 164 can be collectively referred to as a computing entity. The processor 162 can be, for example, a general purpose processor, a Field Programmable Gate Array (FPGA), an Application Specific Integrated Circuit (ASIC), a Digital Signal Processor (DSP), and/or the like. The processor 162 can be configured to retrieve data from and/or write data to memory, e.g., the memory 164, which can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. The processor 162 and memory 164 are configured to select exposure times for the detector 120, receive images from the detector 120, select images received from the detector 120 for analysis, and/or calculate concentrations and/or quantities of analyte populations as described in further detail herein.

In some embodiments described herein a chemiluminescence agent (e.g., luminol) is injected into the capillary before the capillary is imaged and/or before each image of the capillary is captured. Similarly stated, the instrument can include a luminol injector 115. The processor 162 can be operable to cause luminol (or any other suitable chemiluminescence agent) to flow from the luminol injector 115 and through the capillary. The capillary 110 can contain HRP, which may be coated to the walls of the capillary 110. The analyte (or populations of the analyte) can be configured to link to the HRP to form HRP-conjugated analytes. After the luminol is injected, the luminol diffuses to the wall of the capillary and reacts with the HRP-conjugated analytes, releasing photons, which can be detected by the detector 120. Photons released by this enhanced chemiluminescence (ECL) reaction of luminol and HRP are indicative of populations of analytes.

A typical inner diameter (ID) of a capillary is 100 µm and a typical length is 5 cm so the luminol only diffuses a small fraction along the length of the capillary over the time the detector 120 takes a measurement (e.g., an exposure) but has many collisions with the wall of the capillary. Therefore, a local signal is indicative of a local presence of HRP-conjugated analytes, but independent of other signals or the presence of other analytes along the length of the capillary that are more than approximately 1 mm away. Similarly stated, in instances in which peak 152 is more than about 1 mm from peak 154, the intensity of light emitted from peak 152 is independent from the intensity of light emitted from peak 154.

The initial light intensity (photons/second) of an ECL reaction is proportional to an amount of protein (e.g., an analyte) at a particular location within the capillary (e.g., a peak). Accordingly, if the initial light intensity can be determined, the protein concentration and/or quantity can be determined. A number of challenges can present difficulties in accurately determining the initial light intensity, however. Because luminol is consumed by the chemiluminescence reaction, in cases in which there is a small amount of luminol available, such as in capillary-based techniques, the initial light intensity is often determined by measuring light intensity at a number of times and determining the initial light intensity by analyzing the decay curve. A detector can be used to take many exposures and fit a curve to the intensity versus time and extrapolate back to the initial time. For low concentrations of protein, it is desirable to take relatively long exposures, because the total intensity is lower and the decay of chemiluminescence slower. For high concentrations of protein, however, it is desirable to take short exposures, because the total intensity is higher and the decay of chemiluminescence faster. In many instances, however, a capillary may contain a high concentration of protein in one region, and a low concentration of protein in another, perhaps nearby, region. In such an instance, if long exposures are taken, areas of high concentration can "burn out" consuming all or most available luminol during the course of an exposure resulting in false low-concentration readings and/or masking nearby low-concentration signals. Conversely, short exposures are susceptible to be influenced by significant statistical error for low protein concentrations. A need therefore exists to for systems and methods with for accurately determining the quantity of proteins with a high dynamic range. Similarly stated, a need exists to accurately characterize a column (e.g., a capillary) which contains regions having both high concentrations of proteins and low concentrations of proteins. The instrument described above with reference to FIG. 1 can be operable to perform methods that accurately determine the quantity and/or concentration with a high dynamic range.

Figure 2:
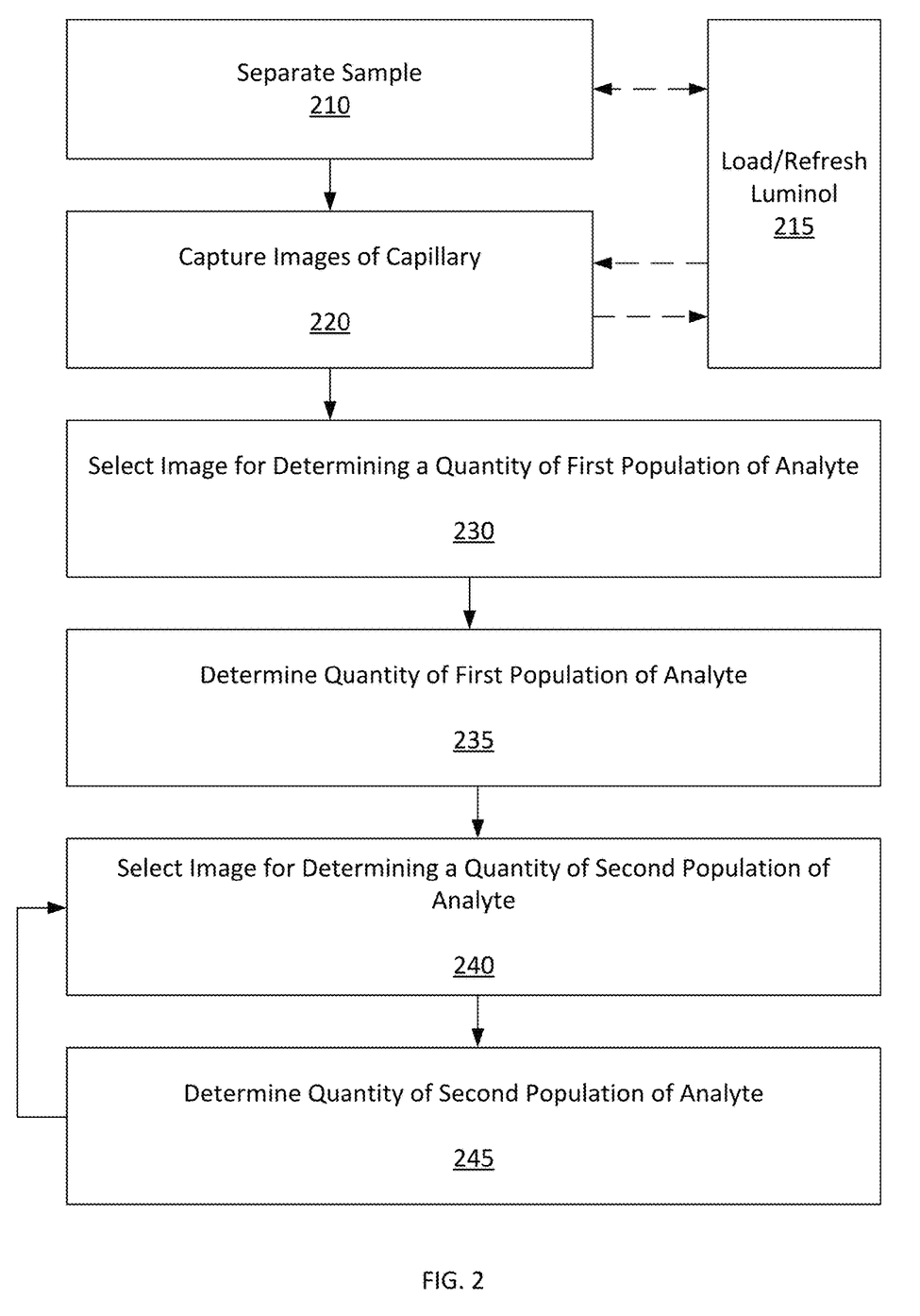
FIG. 2 is a flow chart of a method for measuring concentrations and/or quantities of analyte populations, according to an embodiment.

FIG. 2 is a flow chart of a method for determining the quantity and/or concentration of analytes, according to an embodiment. The method of FIG. 2 can be performed by the instrument described above with reference to FIG. 1. The method includes separating the sample, at 210, loading the sample with luminol, at 215, and capturing images of the capillary, at 220.

In some embodiments, luminol can be loaded into the capillary a number of times, at 215. Each time the capillary is loaded with luminol at least one exposure can be captured, at 220. The length of exposures can vary. For example, the exposure duration can double each time the capillary is loaded with luminol, such as from 1 sec to 2 sec to 4 sec, and so forth up to 256 sec or any other suitable maximum exposure duration. Any suitable progression of exposure duration is possible. For example, each exposure can have a duration that is any integer multiple (or any other multiple) of the previous exposure duration.

Varying the exposures times can produce at least one exposure that is suitable for any concentration of protein that has a good signal to noise with a very small amount of signal decay (i.e., the integrated signal versus exposure duration is still linear). Similarly stated, high exposure durations can be particularly well suited for characterizing low protein concentrations, while low exposure durations can be suitable for characterizing high protein concentrations. In some instances, hardware and/or run time constraints can limit the bounds of the exposure durations. For example, extremely low concentration can be limited by the maximum exposure duration, while extremely high concentration can be limited by the minimum exposure duration.

Thus, at 230, a first image for determining a concentration and/or quantity of a first population of an analyte can be selected. The first population of the analyte can be disposed at a first location along the capillary. In some embodiments, once a signal indicative of the first population of proteins is detected, the detector can continue to capture data (e.g., photons) until a pre-determined threshold is exceeded (e.g., 25,000 counts). In such an embodiment, the exposure time is determined by the time needed to reach the pre-determined threshold. In other embodiments, a series of exposure durations (e.g., 1 sec, 2, sec, 4, sec, 8 sec, etc.) can be predetermined, as discussed above. Regardless of how exposure durations are determined, the first image for determining the quantity of the first population of the analyte can be selected by identifying the image that has the shortest exposure duration in which a signal at the first location exceeds a pre-determined intensity threshold. As discussed above, the initial intensity of an enhanced chemiluminescence reaction is indicative of a quantity and/or concentration of analytes at the location. Therefore, at 235, the quantity of the first population of analyte can be determined by dividing the intensity of the signal detected in the first image (photons or counts) by the exposure duration (seconds).

Selecting an image for determining a concentration and/or quantity of a population of the analyte can be repeated for each location along the capillary having a peak. For example, a second population of analytes can be disposed at a second location. A second image can be selected at 240 by identifying the image in which the signal for the second location exceeds the pre-determined intensity threshold. That signal detected in the second image can be divided by the exposure duration of the second image, and the quantity of the second population of analyte can be determined, at 245.

An image can be selected in this manner for each peak or band and a concentration and/or quantity of analyte within each peak can be determined in a similar manner. Selecting an image in which a signal associated with a particular peak exceeds a predetermined threshold can mitigate the tradeoffs inherent in selecting an appropriate exposure time to which known ECL techniques are subject. For example, a very short exposure time (e.g., 1 second) can be used to determine a quantity of the peak with the highest initial intensity (and hence concentration and/or quantity). Such a short exposure may be too short to determine the quantity of other peaks in the capillary. Similarly stated, other peaks may be at or below the detection threshold of an image with a short exposure time and/or may have low signal to noise ratios. As another example, a relatively long exposure time (e.g., 64 seconds) can be used to determine a quantity of a peak with low initial intensity (and hence concentration and/or quantity). Such a long exposure may be unsuitable for determining the concentration and/or quantity of other peaks having higher concentrations and/or quantities of analytes. For example, over a 64 second measurement (exposure), high-intensity peaks may consume all locally available luminol and/or significant non-linearity of high-intensity decay may introduce relatively large measurement errors.

In some instances, the shortest nominal exposure duration can be selected by selecting the shortest exposure for which at least one peak is above a predetermined count threshold. The predetermined count threshold can be related to the initial luminol concentration that can be uniform throughout the capillary and independent of any specific subpopulation concentration. At this predetermined count threshold signals exceeding the predetermined threshold will typically have a suitable signal to noise ratio without significant signal decay.

As discussed above, multiple images of the capillary can be captured, and the images can have different durations. In some instances a series of exposures in which each exposure has the same or approximately the same exposure duration can be taken. The first series of exposures can have, for example, the shortest nominal exposure duration. For example, each exposure from the first series of exposures can have an exposure duration of 1 sec. The second series of exposures can each have, for example, an exposure duration of 2 sec, and so forth. In some instances the exposure duration of each exposure from a series of exposures can vary from the nominal exposure duration. For example, in an instance where the second series of exposures has a nominal exposure duration of 2 sec, exposures can be captured having exposure durations of 1.6 sec, 1.8 sec, 2.0 sec, 2.4 sec, and so forth. Similarly stated, the exposure duration for exposures from a series of exposures can be weighted around the nominal exposure duration for that series. In this way, the transition from one nominal exposure duration to another nominal exposure duration can be smoothed. As described in further detail herein, the light intensity can be determined by dividing the integrated signal (detected photons and/or counts) by the actual exposure duration.

Some embodiments described herein employ a mathematical model of luminol diffusion and reaction in a round capillary shown below that predicts the luminol concentration as a function of time (t) and radial location (r) within the capillary as well as for different ratios of reaction rate to diffusivity (mass transfer Biot number, Bi) for a capillary having a radius (b). The model shows that if the integrated signal is measured when ~15% of the luminol has been consumed (i.e. at 15% of the maximum integrated signal), then the error in approximating the initial reaction rate (proportional to the target protein concentration) is within in narrow range (15-25%) for Bi<0.5. For Bi<0.1, the error is equal to % consumed luminol (reaction-limited process). Only ratios of target concentrations are meaningful (the units are arbitrary), so any fixed error percentage cancels in such a ratio.

$$c'(Bi, t, r) = \frac{c}{c_0} =$$

$$2 \cdot \sum_{n=1}^{\infty} e^{-\beta_n^2 \cdot \frac{t}{\tau}} \cdot \frac{\beta_n \cdot J_1(\beta_n) \cdot J_0\left(\beta_n \cdot \frac{r}{b}\right)}{(Bi^2 + \beta_n^2) \cdot (J_0(\beta_n))^2} - \beta_n \cdot J_1(\beta_n) + Bi \cdot J_0(\beta_n) = 0$$

$$\tau = \frac{t \cdot D}{b^2}$$

$$\frac{c_{avg}}{c_0} = \frac{1}{\pi} \cdot \int_0^1 c'(Bi, t, r') \cdot 2 \cdot \pi \cdot r' dr'$$

$$target_{concentration} \sim \frac{d}{dt} c'(Bi, 0, 1)$$

Figure 6:
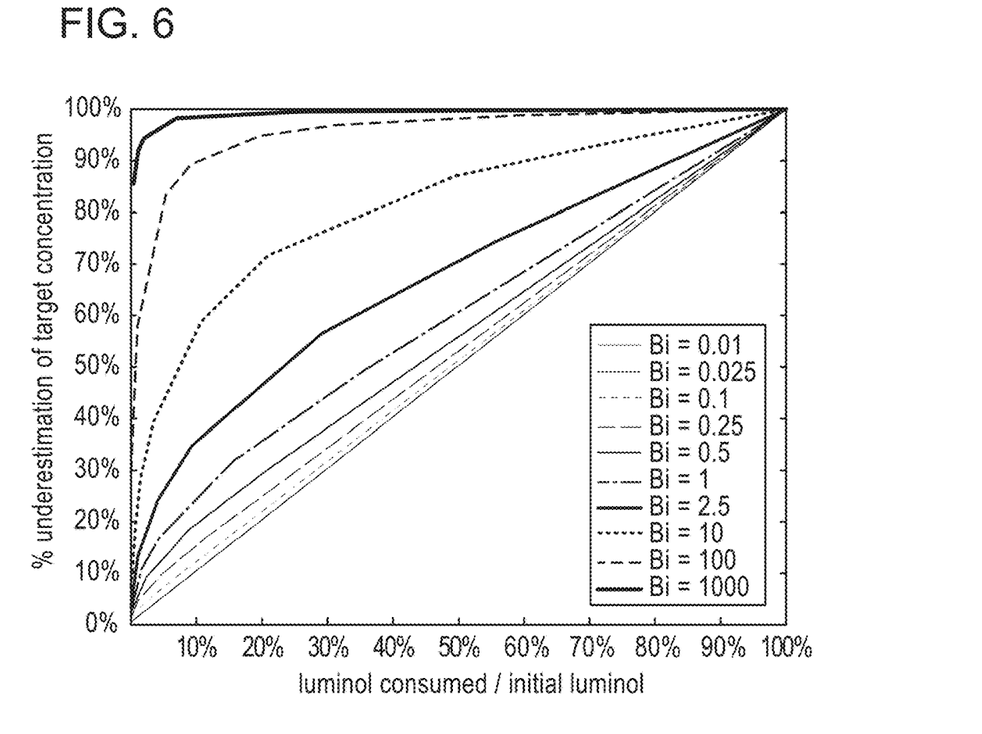
FIG. 6 is a plot of a simulation of measurement error based on luminol consumption and mass transfer coefficient, according to an embodiment.

$D$ is diffusivity coefficient $Bi$ is mass transfer Biot number $b$ is capillary radius The above model and FIG. 6, discussed in further detail herein, demonstrate that by selecting an image for each population of an analyte (e.g., each location along a capillary) in which the signal exceeds a predetermined threshold, the decay over the exposure time for that signal can be approximated as linear. Therefore, the initial intensity can be calculated by dividing the intensity for that image by the exposure duration.

The actual decay over the exposure period is exponential. Therefore, the higher the predetermined threshold, the less accurate the linearizing approximation becomes. The lower the predetermined threshold, however, and the lower the signal-to-noise ratio. Selecting an appropriate predetermined threshold is therefore a balance between linearity and noise. Table 1, shown below, presents experimental data used to select an appropriate predetermined threshold. The experimental data reveals that selecting a predetermined threshold for signal intensity that is approximately 25% of the saturation level for the sensor results in a ratio of linear slope to the actual decay below 0.89, which is a suitable tradeoff. Other suitable thresholds could be between 30% of the saturation level for the sensor to 20% of the saturation level of the sensor.

TABLE 1

| Time/Lambda | Rate | Ratio Slope |
|---|---|---|
| 0.025 | 0.02469008797 | 0.9876035189 |
| 0.05 | 0.0487705755 | 0.97541151 |
| 0.075 | 0.07225651367 | 0.9634201823 |
| 0.1 | 0.09516258196 | 0.9516258196 |
| 0.15 | 0.1392920236 | 0.9286134905 |
| 0.2 | 0.1812692469 | 0.9063462346 |
| 0.25 | 0.2211992169 | 0.8847968677 |
| 0.3 | 0.2591817793 | 0.8639392644 |
| 0.35 | 0.2953119103 | 0.8437483151 |
| 0.4 | 0.329679954 | 0.8241998849 |
| 0.5 | 0.3934693403 | 0.7869386806 |

To minimize spatial variation of linearization errors (and resulting discontinuous jumps in the intensity curve), an additional interpolation step can be employed. Signals captured in multiple images having discrete exposure times can be used. After selecting the image in which a signal is closest to the predetermined threshold (or the image with the shortest exposure time in which the signal exceeds the predetermined threshold), additional images, such as the immediately prior and/or subsequent images (e.g., images having the next-longer and/or next-shorter exposure duration) be analyzed and used to interpolate to a predicted exposure time that would yield the target threshold value. Similarly stated, a predicted exposure time to reach the predetermined threshold can be calculated. The predicted exposure time may not correspond to an exposure time of any actually captured image. In such an embodiment, calculating the initial intensity can be performed by dividing the predetermined threshold by the predicted exposure time. In some embodiments, the predicted exposure time can be calculated by linearly interpolating between a measurement that is just below the predetermined threshold and a measurement just above the predetermined threshold.

EXAMPLE 1

Figure 3:
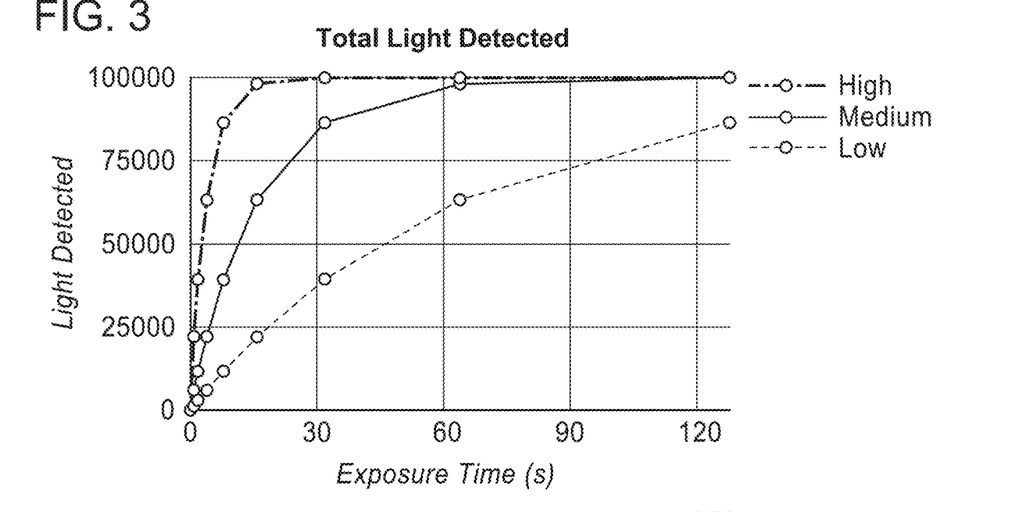
FIG. 3 is a plot of a simulation of light produced by an ECL technique detected over time.

FIG. 3 depicts simulated signal levels using the techniques described herein. FIG. 3 depicts three intensity levels, "low," "medium," and "high." The medium intensity level has an intensity four times the intensity of the low intensity level, and the high intensity level has an intensity four times the intensity of the medium intensity level. The predetermined count threshold can be 25,000, which can be determined, for example, based on detector sensitivity and/or saturation as discussed above. Similarly stated, a count threshold of 25,000 may be 25% of the saturation level for the sensor. A nominal exposure duration of 16 sec can be selected for the low intensity signal, a nominal exposure duration of 4 sec can be selected for the medium intensity signal, and a nominal exposure duration of 1 sec can be selected for the high intensity signal. The intensities (photons/second) are determined by dividing the integrated signals by the exposure duration.

TABLE 2

| Signal Input | Exposure < 25,000 | Signal measured | Intensity |
|---|---|---|---|
| High | 1 sec | 22,000 | 22.000/1 = 22,000 |
| Medium | 4 sec | 22,000 | 22.000/4 = 5,500 |
| Low | 16 sec | 22,000 | 22.000/16 = 1,375 |

EXAMPLE 2

Figure 4:
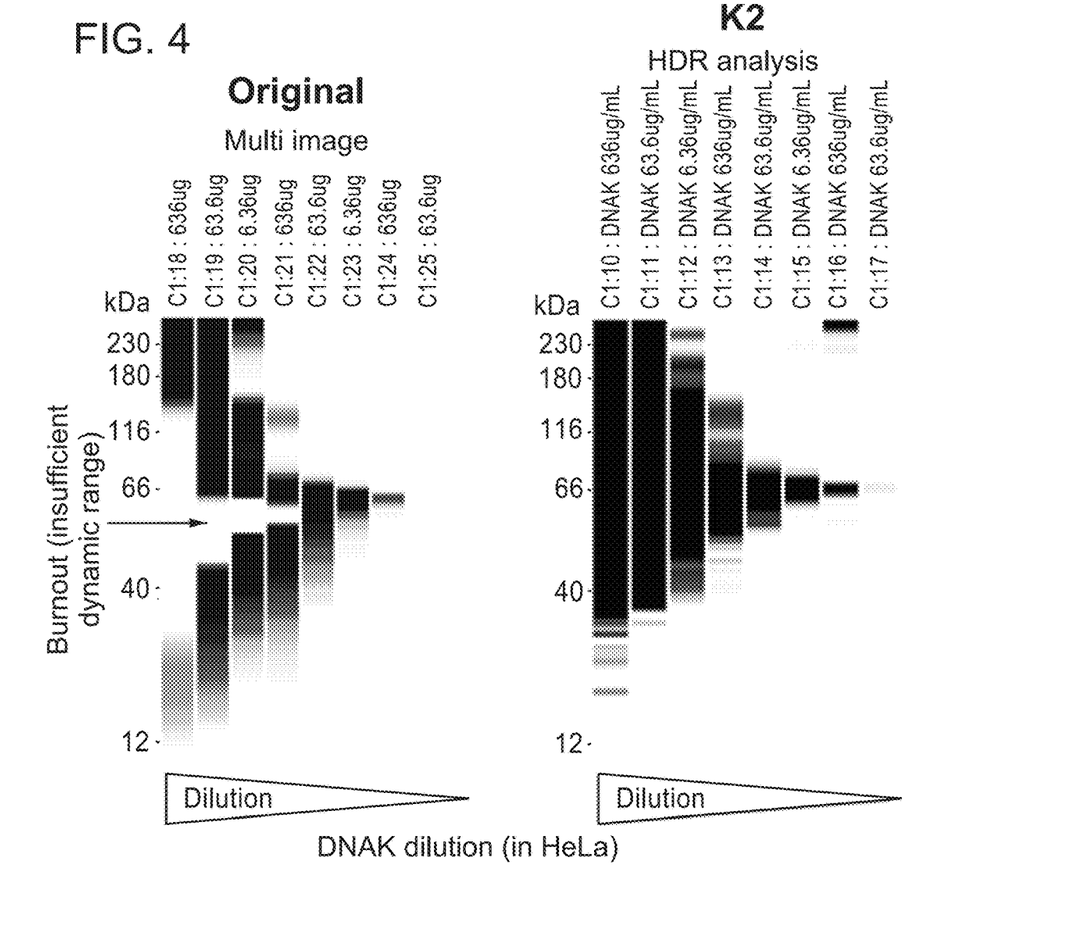
FIGS. 4 and 5 depicts a comparison of known techniques for measuring a concentration and/or quantity of an analyte and a method of measuring a concentration and/or quantity of an analyte according to methods described herein.
Figure 5:
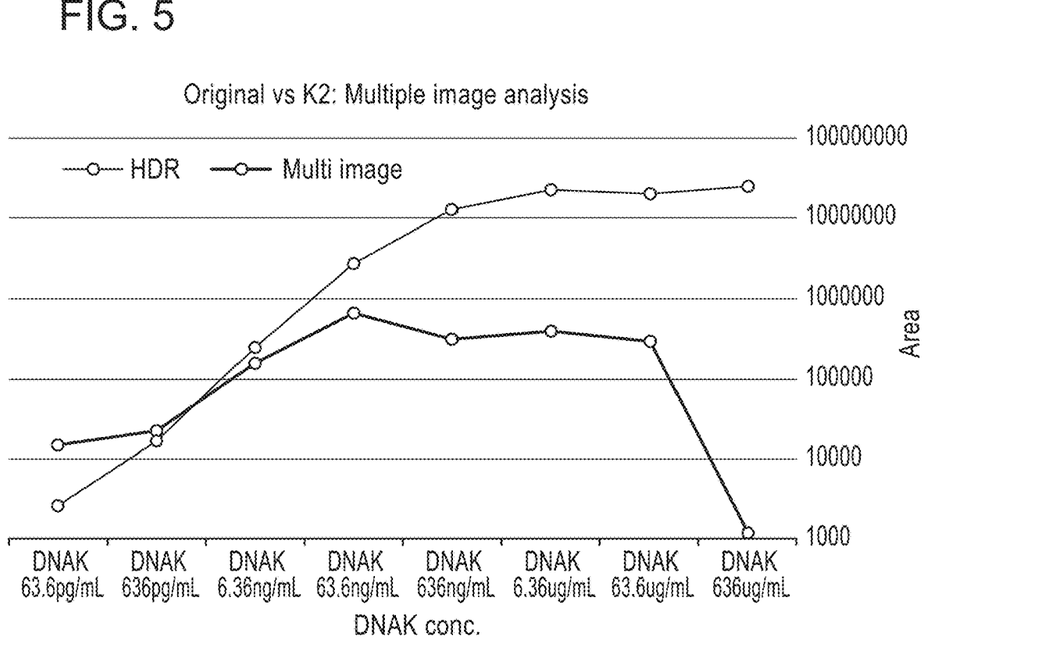

Techniques described herein can increase the dynamic range of protein concentration analyses as compared to known techniques. For example, FIGS. 4 and 5 illustrates a known method of determining protein concentration labeled "Multi image" which depict a "burnout" phenomenon that occurs when a large range of protein concentrations are processed. Burnout occurs due to high concentrations of protein consuming available luminol in the chemiluminescence reaction during the measurement (exposure) that is suitable for accurately resolving low protein concentrations. Similarly stated, the exposure duration needed to resolve the low protein concentrations is too long to detect the decay of the chemiluminescence for high protein concentrations.

FIGS. 4 and 5 also illustrates a "HDR" (high dynamic range) analysis using techniques described herein. The HDR analysis illustrates that both high concentrations (636 μg/mL) and low concentrations (63.6 μg/ml) of protein can be detected without the large systematic under estimation of high signal illustrated by the Original Multi image technique.

As described above, burnout can adversly effect known techniques for determining protein concentration. Techniques described herein may, however, benefit from burnout. For example, because luminol diffuses very slowly within a capillary, when exposure duration is incresed from short to long, the short durations can be used to accurately quantify areas with high concentrations of protein. As the exposure duration increases, areas with high protein concentrations may have depleted available luminol. As a result, a nearby low concentration signal with a lower intensity that would otherwise have been masked by the brighter signal assocaited with the high concentration (e.g., sensor blinding) may be resolvable and/or more accurately detected during a longer duration exposure captured after the high concentration has consumed locally available luminol. In instances in which high concentration peaks are relatively close to low concentration peaks, it may, therefore, be desirable to capture multiple images without refreshing luminol.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

While the embodiments have been particularly shown and described, it will be understood that various changes in form and details may be made. Although various embodiments have been described as having particular features and/or combinations of components, other embodiments are possible having a combination of any features and/or components from any of embodiments as discussed above. For example, in some embodiments, luminol can be refreshed between series of exposures, for example, by flowing luminol into a capillary between exposures and/or by continuously flowing luminol into the capillary. In some instances, flow within the capillary can be prevented while an exposure is being taken, for example, by balancing hydrostatic pressure at either end of the capillary, by eliminating electrophoretic processes during imaging, etc.

What is claimed is:

1. A method, comprising:
   separating a plurality of populations of proteins to a plurality of locations along a length of a capillary via electrophoresis;
   loading the capillary with a detection agent that is capable of causing a signal indicative of a quantity of protein at each location from the plurality of locations along the length of the capillary, the signal changing with time;
   capturing a first image of the capillary containing the proteins and the detection agent, the first image captured over a first duration, the first duration being associated with a first rate of change of the signal at the first location from the plurality of locations during the first duration;
   capturing a second image of the capillary containing the proteins and the detection agent, the second image captured over a second duration different than the first duration, the second duration being associated with a second rate of change of the signal at a second location from the plurality of locations during the second duration;
   determining a quantity of a first population of proteins at the first location using the first image, the first population of proteins being from the plurality of populations of proteins; and
   determining a quantity of a second population of proteins at the second location using the second image, the second population of proteins being from the plurality of populations of proteins.

2. The method of claim 1, wherein the detection agent is one of a chemiluminescence agent or a chromogenic agent.

3. The method of claim 1, further comprising:
   refreshing the detection agent between capturing the first image and capturing the second image.

4. The method of claim 1, further comprising:
   measuring, while capturing the first image, a length of time until a predetermined signal strength threshold is exceeded, the first duration being the length of time.

5. The method of claim 1, further comprising:
   measuring, while capturing the first image, a length of time until a predetermined signal strength threshold is exceeded, the first duration being the length of time, the second duration being an integer multiple of the first duration.

6. The method of claim 1, wherein the quantity of the first population of proteins is at least three times greater than the quantity of the second populations of proteins, the method further comprising:
   refreshing the detection agent between capturing the first image and capturing the second image, the quantity of the first population of proteins being sufficient to consume a quantity of detection agent at the first location during the second duration.

7. The method of claim 1, wherein:
   the quantity of the first population of proteins is at least three times greater than the quantity of the second population of proteins; and
   a signal indicative of the quantity of the second population of proteins at the second location is too faint to determine the quantity of the second population of proteins based on the first image.

8. The method of claim 1, further comprising:
capturing a plurality of images additional to the first image and the second image, each image from the plurality of images captured over a duration that is longer than a duration over which an immediately previous image from the plurality of images was captured; and
selecting an image from the plurality of images to determine a quantity of a population of proteins at each location from the plurality of locations that contains proteins, each image selected based on a signal for that location exceeding a common predetermined signal strength threshold.

9. The method of claim 1, further comprising:
capturing a plurality of images additional to the first image and the second image, each image from the plurality of images captured over a duration that is longer than a duration over which an immediately previous image from the plurality of images was captured; and
selecting an image from the plurality of images to determine a quantity of a population of proteins from the plurality of populations of proteins at each location from the plurality of locations that contains proteins, each image selected based on a signal for that location exceeding a common predetermined signal strength threshold;
calculating a predicted exposure time for a signal associated with the first location to exceed the predetermined threshold based on the first image, a third image captured immediately prior to the first image, and a fourth image captured immediately subsequent to the first image;
calculating an initial intensity of the signal associated with the first location by dividing the predetermined threshold by the predicted exposure time, the quantity of the first population of proteins determined based on the initial intensity of the signal associated with the first location.

10. The method of claim 1, wherein, the first location of the capillary has a highest concentration of proteins in the capillary, the method further comprising:
measuring, while capturing the first image, a length of time until a predetermined signal strength threshold is exceeded, the first duration being the length of time, the first image being first in a plurality of images, the plurality of images including the second image.

11. The method of claim 1, wherein the detection agent is luminol.

12. The method of claim 1, wherein:
the quantity of the first population of proteins is at least ten times greater than the quantity of the second population of proteins, the method further comprising:
identifying a first optical signal represented in the first image and indicative of the quantity of the first population of proteins, a strength of the first optical signal exceeding a predetermined threshold;
determining an initial intensity of the first optical signal by dividing the strength of the first optical signal by the first duration, the quantity of the first population of proteins calculated based on the initial intensity of the first optical signal; and
identifying a second optical signal represented in the second image and indicative of the quantity of the second population of proteins, a strength of the second optical signal exceeding the predetermined threshold.

13. The method of claim 12, further comprising:
determining an initial intensity of the second optical signal by dividing the strength of the second optical signal by the second duration, the quantity of the second population of proteins calculated based on the initial intensity of the second optical signal.

14. The method of claim 12, further comprising:
capturing a plurality of images additional to the first image and the second image, the plurality of images being divided into subsets each having a nominal duration, wherein a duration of each image from each subset varies by 50% or less from the nominal duration for that subset.

15. The method of claim 12, further comprising:
capturing a plurality of images additional to the first image and the second image;
dividing the plurality of images into subsets wherein each subset of images from the plurality of images has a nominal duration of twice a nominal duration of an immediately prior subset of images from the plurality of images.

16. The method of claim 12, further comprising:
capturing a plurality of images additional to the first image and the second image, each image from the plurality of images captured over a duration that is at least twice a duration over which an immediately prior image from the plurality of images was captured.

17. The method of claim 12, further comprising:
adding one of a chemiluminescence agent or a chromogenic agent to the capillary prior to capturing the first image and the second image.

18. The method of claim 1, wherein the second duration is longer than the first duration.

19. The method of claim 1, the method further comprising:
capturing a plurality of images including the first image and the second image, each image from the plurality of images captured over a duration that is different than each duration over which the remaining images from the plurality of images were captured, each image from the plurality of images including a representation of an optical signal from a plurality of optical signals, each optical signal from the plurality of optical signals associated with a population of proteins; and
determining the quantity of the first population of proteins at the first location includes:
selecting the first image based on a first optical signal from the plurality of optical signals that is represented in the first image exceeding a threshold such that the first optical signal can be approximated as linear during the first duration, the first optical signal associated with the first population of proteins;
determining the quantity of the first population of proteins based on a linear approximation of the of the first optical signal; and
determining the quantity of proteins at the second location includes:
selecting the second image based on a second optical signal from the plurality of optical signals that is represented in the second image exceeding the threshold such that the second optical signal can be approximated as linear during the second duration, the second optical signal associated with the second population of proteins;
determining the quantity of the second population of proteins based on a linear approximation of the of the second optical signal.

20. A method, comprising:
separating a sample containing a first population of proteins and a second population of proteins to a first location and a second location, respectively, along a length of a capillary via electrophoresis;
loading the capillary with a detection agent that is capable of causing a signal indicative of a quantity of protein along a length of the capillary, the signal changing with time;
capturing a first image of the capillary containing the proteins and the detection agent, the first image captured over a first duration, the first duration selected based on a first signal crossing a predetermined signal threshold, the first signal being associated with the first population of proteins;
capturing a second image of the capillary containing the proteins and the detection agent, the second image captured over a second duration different than the first duration, the second duration being selected based on a second signal crossing the predetermined signal threshold, the second signal associated with the second population of proteins;
determining a quantity of the first population of proteins using the first image; and
determining a quantity of the second population of proteins using the second image.

\* \* \* \* \*